(12) United States Patent
Rosenfeld

(10) Patent No.: US 6,821,270 B2
(45) Date of Patent: Nov. 23, 2004

(54) SANITARY ABSORBENT ARTICLE

(75) Inventor: Leonard G. Rosenfeld, Yardley, PA (US)

(73) Assignee: McNeil-PPC, Inc., Skillman, NJ (US)

( * ) Notice: Subject to any disclaimer, the term of this patent is extended or adjusted under 35 U.S.C. 154(b) by 0 days.

(21) Appl. No.: 10/075,487

(22) Filed: Feb. 13, 2002

(65) Prior Publication Data

US 2003/0153890 A1 Aug. 14, 2003

(51) Int. Cl.[7] .................................................. A61F 13/15
(52) U.S. Cl. ........................... 604/385.04; 604/385.05; 604/385.01; 604/1; 604/386; 604/385.201
(58) Field of Search ................ 604/385.01, 385.04, 604/386, 385.05, 385.23, 387, 385.201

(56) References Cited

U.S. PATENT DOCUMENTS

| | | | |
|---|---|---|---|
| 2,787,271 A | 4/1957 | Clark | |
| 3,397,697 A | 8/1968 | Rickard | |
| 4,285,343 A | 8/1981 | McNair | |
| 4,589,876 A | 5/1986 | Van Tilburg | |
| 4,608,047 A | 8/1986 | Mattingly | |
| 4,687,478 A | 8/1987 | Van Tillburg | |
| 4,900,320 A | 2/1990 | McCoy | |
| 4,917,697 A | 4/1990 | Osborn, III et al. | |
| 5,683,373 A | * 11/1997 | Darby | 604/385.1 |
| 5,713,886 A | * 2/1998 | Sturino | 604/390 |
| D445,181 S | * 7/2001 | Kramer | D24/125 |
| D445,498 S | * 7/2001 | Renz et al. | D24/125 |
| 2002/0128622 A1 | 9/2002 | Canelho et al. | |

FOREIGN PATENT DOCUMENTS

| | | | | |
|---|---|---|---|---|
| DE | 10144908 | 10/2002 | | |
| EP | 1133961 | * 9/2001 | | A61F/13/15 |
| EP | 1138594 | * 10/2001 | | A61F/13/15 |
| WO | WO 00/72790 A1 | 12/2000 | | |
| WO | WO 0135888 | 5/2001 | | |
| WO | WO 01/68024 | * 9/2001 | | A61F/13/15 |
| WO | WO 0178838 | 10/2001 | | |

* cited by examiner

Primary Examiner—John J. Calvert
Assistant Examiner—Jacqueline F. Stephens

(57) ABSTRACT

A sanitary napkin adapted to be worn in a thong undergarment. The sanitary napkin includes a central absorbent pad having a liquid pervious cover layer, a liquid impervious barrier layer and an absorbent core between the cover layer and barrier layer. The sanitary napkin has a first distal end region, an opposite second distal end region and a central region intermediate the first distal end region and the second distal end region and a flap extending laterally outward from each longitudinal side edge of the sanitary napkin in the central region. The absorbent core has a maximum width in the first distal end region that does not exceed 40 mm and a ratio of a length of the first distal end region to the maximum width of the absorbent core in the first distal end region is less than 2.

10 Claims, 4 Drawing Sheets

US 6,821,270 B2

SANITARY ABSORBENT ARTICLE

FIELD OF THE INVENTION

The present invention relates to disposable absorbent articles, such as sanitary napkins, panty liners, and the like that are adapted to be worn in a thong style undergarment.

BACKGROUND OF THE INVENTION

Sanitary napkins having side flaps are disclosed in the literature and are commercially available in the marketplace. Generally, the flaps extend laterally from the side edges of a central absorbent structure and are intended to drape over the edges of the wearer's panties in the crotch region. Thus, the flaps are disposed between the edges of the wearers panties in the crotch region and the wearer's thighs. Commonly, the flaps are provided with an attachment means for affixing the flaps to the underside of the wearer's panties.

The flaps serve at least two purposes. First, the flaps prevent exudates from soiling the edges of the wearer's panties and second, the flaps, when affixed to the underside of the panties, help stabilize the napkin in the undergarment and prevent it shifting out of place. Typically, the flaps extend only from a central region of the sanitary napkin rather than along the entire length of the sanitary napkin. This enables the flaps to more easily conform to the curved contours of the crotch region of the undergarment. That is, since the crotch portion of an undergarment is curved, the length of the flaps cannot extend along the entire length of the napkin since they will not effectively wrap around the panty crotch.

Sanitary napkins having flaps are disclosed in U.S. Pat. No. 4,687,478, entitled "Shaped Sanitary Napkin With Flaps", to Van Tilburg on Aug. 18, 1987, U.S. Pat. No. 4,608,047, entitled "Sanitary Napkin Attachment Means", to Mattingly on Aug. 26, 1986, U.S. Pat. No. 4,589,876, entitled "Sanitary Napkin", to Van Tilburg on May 20, 1986, U.S. Pat. No. 4,285,343, entitled "Sanitary Napkin", to McNair on Aug. 25, 1981, U.S. Pat. No. 3,397,697, entitled "Disposable Sanitary Shield For Undergarments", to Rickard on Aug. 20, 1968, U.S. Pat. No. 2,787,271, entitled "Sanitary Napkin", to Clark on Apr. 2, 1957 and U.S. Pat. No. 4,900,320, entitled "Sanitary Napkin With Undergarment Gathering Flaps, to McCoy on Feb. 13, 1990, all of which are incorporated herein by reference in their entirety.

As the wearing of thong style undergarments has recently increased, there has also been a need for disposable absorbent articles to be adapted to these types of undergarments. WO 00/72790 A1 discloses an absorbent article which is intended to be worn in a thong undergarment. The absorbent article has a wide end and an narrow end to conform to the shape of a thong undergarment and is provided with fastening tabs in the narrow end of the article. One of the problems with this design is that the narrow end of the absorbent article has a tendency to shift laterally as a wearer of the article moves. Due to its width, the rear section of the napkin is mechanically less stable than the wider rear section of a conventional sanitary napkin

SUMMARY OF THE INVENTION

It is an object of the present invention to provide a sanitary napkin having flaps that is adapted for use in a thong style of women's undergarment.

In accordance with the present invention, there has been provided a sanitary napkin adapted to be worn in a thong undergarment comprising a central absorbent pad, the central absorbent pad having a liquid pervious cover layer, a liquid impervious barrier layer and an absorbent core between the cover layer and barrier layer. The sanitary napkin has a pair of opposite longitudinal side edges defining therebetween a width dimension, a first transverse end and an opposite second transverse end defining therebetween a length dimension. The sanitary napkin has a longitudinal centerline, a lateral centerline, a first distal end region, an opposite second distal end region and a central region intermediate the first distal end region and the second distal end region. The sanitary napkin further having a flap extending laterally outward from each longitudinal side edge in the central region along a line of juncture, the line of juncture defining the length of the central region, each flap being adapted to fold over a crotch portion of the thong undergarment in use. The width of the absorbent core varies along at least a portion of the length of the absorbent core such that the width of the absorbent core in the second distal end region has a maximum value that is greater than a maximum value of the width of the absorbent core in the first distal end region. The absorbent core in the first distal end region has a length measured intermediate the central region and the first transverse end, wherein the maximum value of the width of the absorbent core in the first distal end region does not exceed 40 mm along any portion of the length of the first distal end region, the width of the absorbent core in the first distal end region does not exceed 30 mm along at least one half of the length of the first distal end region and wherein a ratio of the length of the first distal end region to the maximum width of the absorbent core in the first distal end region is less than 2.

These and other objects of the present invention will be more readily apparent when considered in reference to the following description and when taken in conjunction with the accompanying drawings. It is to be understood, however, that the drawings are provided for purposes of illustration only and not as a definition of the boundaries of the invention, for which reference should be made to the appending claims.

DETAILED DESCRIPTION

Figure 1:
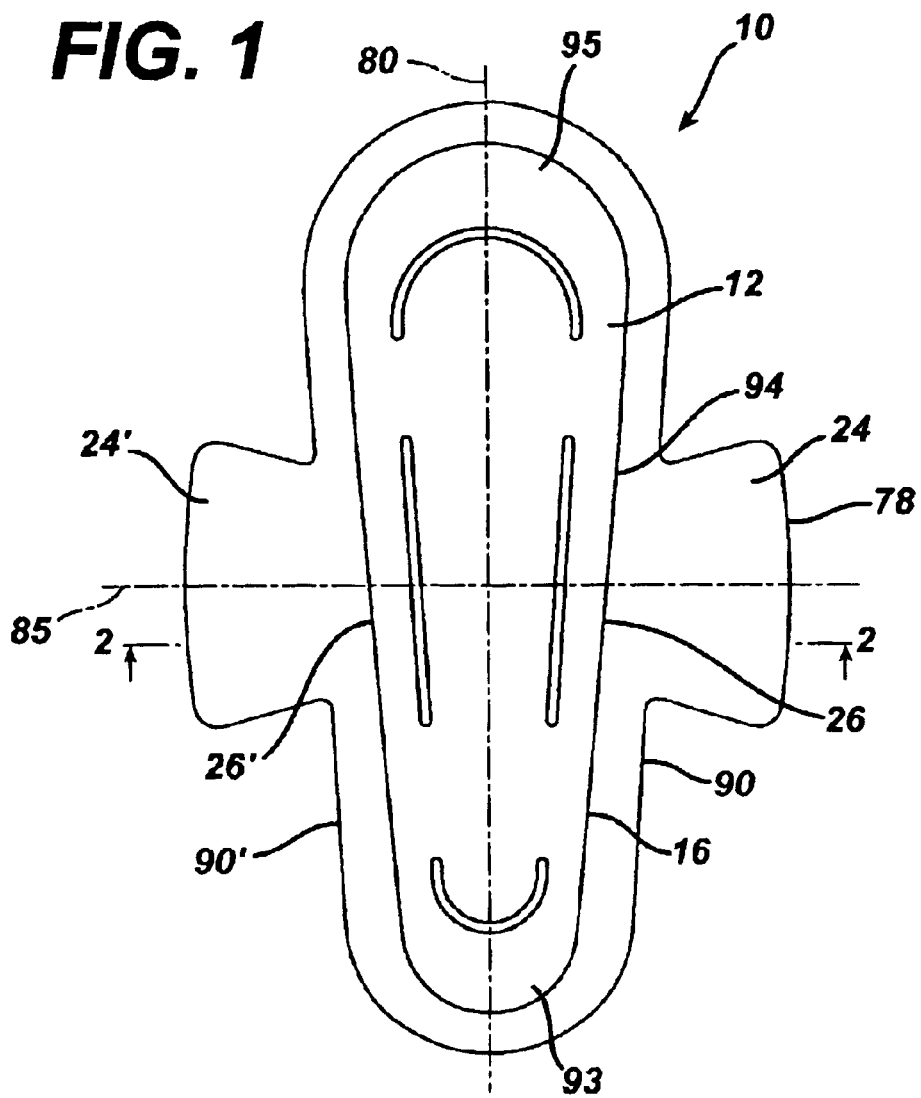
FIG. 1 is a top plan view of a sanitary napkin according to the present invention.

The present invention relates to sanitary napkins adapted to be worn in a crotch portion of a wearer's thong style undergarment in use. The napkin comprises a central absorbent pad having a liquid pervious cover layer, a liquid impervious barrier layer and an absorbent core between the cover layer and barrier layer. The central absorbent pad will generally have an absorbent capacity sufficient to absorb the anticipated total amount of menstrual fluid. Central absorbent pad, is preferably thin, i.e. less than about 5 mm in caliper, preferably between about 2.5 mm and about 4 mm. It has been found that a sanitary napkin having a narrow, thin absorbent core is extremely comfortable to the user.

The sanitary napkin has a longitudinal centerline, a lateral centerline, a pair of opposite longitudinal side edges defining therebetween a width dimension, a pair of opposite transverse ends including a first transverse end and an opposite second transverse end defining therebetween a length dimension. The sanitary napkin is provided with side flaps which extend along a line of juncture from the longitudinal side edges, the line of juncture defining a central region of the sanitary napkin. In a preferred embodiment, one flap extends from each respective longitudinal side edge. The side flaps are adapted to be folded over the edges of a crotch portion of the wearer's undergarment in use. Each flap extends laterally outward from each longitudinal side edge along a line of juncture. The length of the line of juncture defines the length of the central region of the sanitary napkin. In a preferred embodiment, each flap has substantially the identical shape and size as the opposite flap and each flap is spaced equidistant from a respective transverse end, i.e. they have a symmetrical orientation. In an embodiment (not shown) where the flaps are affixed to the sanitary napkin in an asymmetric orientation, the length of the central region is measured from the flap being closer to a respective transverse end region, i.e. the line of juncture being closest to the transverse end region.

The sanitary napkin further includes a first distal end region and an opposite second distal end region, the central region being intermediate the first distal end region and the second distal end region. Since the flaps define the central region, they also accordingly define the first and second distal end regions. More specifically, the first distal end region has a length that extends from the central region to the first transverse end. Similarly, the second distal end region has a length that extends from the central region to the second transverse end. Thus, the first distal end region has a length as measured along the longitudinal centerline from the first distal end to a line perpendicular to the longitudinal centerline at the end of the flap nearest the first distal end to the first distal end. Similarly, the length of the second distal end region is measured from a line perpendicular to the longitudinal centerline from the flap nearest the second distal end to the second distal end.

The absorbent core has two opposite side edges defining therebetween a width of the absorbent core. The width of the absorbent core varies along at least a portion of its length. The width of the absorbent core in the second distal end region has a maximum value that is greater than a maximum value of the width of the absorbent core in the first distal end region. Each side edge is inward from and in close proximity to a respective longitudinal side edge of the sanitary napkin. In a preferred embodiment, as illustrated in FIG. 1, the side edges of the absorbent core extend obliquely with respect to the longitudinal centerline and taper from the wider second distal end region to the narrower first distal end region. In a most preferred embodiment, the width of the absorbent core continuously tapers from a maximum width adjacent the central region to a minimum width adjacent the first distal end.

As used herein, the term "sanitary napkin" refers to an article which is worn by females in an undergarment adjacent to the pudendal region and which is intended to absorb and contain the various exudates which are discharged from the body (e.g., blood menses, and urine) and which is intended to be discarded after a single use (i.e., it is not intended to be laundered or otherwise restored or reused).

A specific example of implementation of a sanitary napkin according to the present invention is illustrated in FIG. 1. The sanitary napkin designated by the reference numeral 10 basically comprises a main body represented by central absorbent pad 12. The central absorbent pad 12 has an imaginary longitudinal centerline 80, an imaginary lateral centerline 85, a pair of opposite longitudinal side edges 90, 90', a first distal end 93 and an opposite second distal end 95 and a central region 94, intermediate the distal ends.

Figure 2:
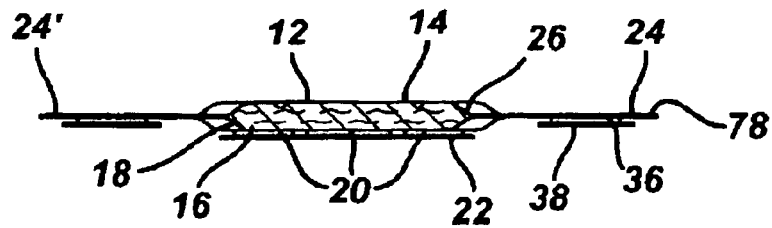
FIG. 2 is a side cut away view of the sanitary napkin of FIG. 1 taken through lines 2—2.

As illustrated in FIG. 2, topsheet 14 and backsheet 18 are joined at seam 39 (also commonly referred to as a flange seal) around the entire periphery of sanitary napkin 10. The purpose of this seam is to unite the various elements of the sanitary napkin into a unitary structure. Seam 39 can be formed by any means commonly used in the art for this purpose such as by gluing, crimping, or heat-sealing. Seam 39 is illustrated extending completely around the periphery of sanitary napkin 10; this is a suitable embodiment for ease of construction.

However, other means of uniting the various elements can be used. The central absorbent pad 12 comprises absorbent core 16, topsheet 14 and backsheet 18, wherein backsheet 18 is disposed on a side of absorbent core 16 that is opposite that of topsheet 14.

Topsheet 14 is liquid permeable and, when sanitary napkin 10 is in use, is in close proximity to the skin of the user. Topsheet 14 is compliant, soft feeling, and non-irritating to the user's skin. It can be made from any of the materials conventional for this type of use. Non-limiting examples of suitable materials that can be used as topsheet 14 are woven and nonwoven fabrics formed from polyester, polypropylene, nylon, and/or rayon fibers or the topsheet may be an apertured thermo-plastic film. Apertured formed films are preferred for topsheet 14 because they are pervious to liquids and yet non-absorbent. Thus, the surface of the formed film that is in contact with the body remains dry and is more comfortable to the wearer.

Backsheet 18 is impervious to liquids and, thus, prevents menstrual fluid from soiling the clothing of the user. Any material used in the art for such purpose can be utilized herein. Suitable materials include embossed or non embossed polyethylene films and laminated tissue.

Absorbent core 16 provides the means for absorbing menstrual fluid. Absorbent core 16 is generally compressible, comfortable and non-irritating to the user's skin. It can comprise any material used in the art for such purpose. Examples include comminuted wood pulp that is generally referred to as airfelt, creped cellulose wadding, absorbent foams, absorbent sponges, absorbent hydrogel materials, polymeric fibers, or any equivalent material or combinations of materials. In a preferred embodiment, as shown in FIG. 1, the absorbent core 16 is wider in the second distal end 95 and tapers continuously towards the first distal end 93.

Figure 3:
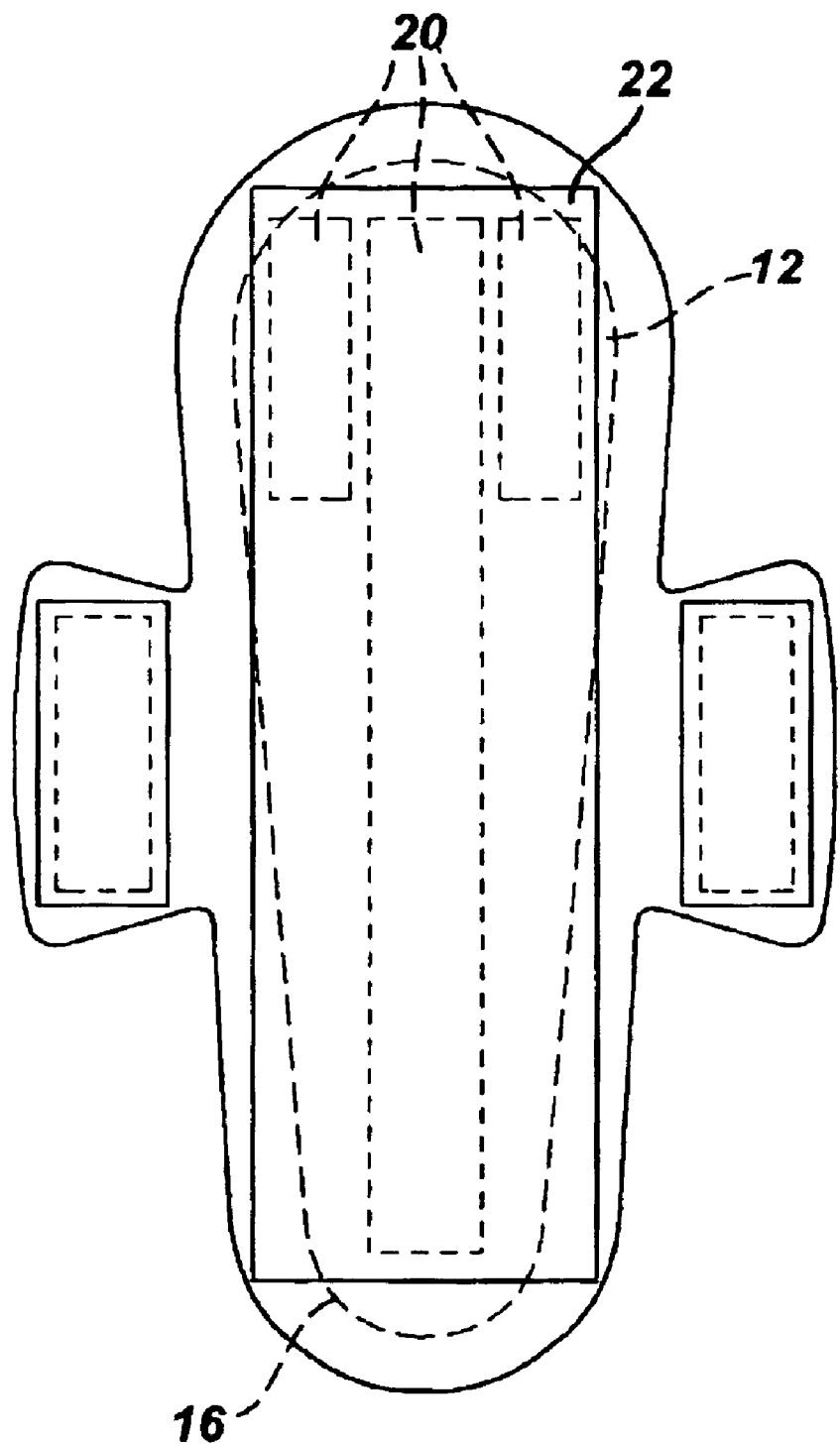
FIG. 3 is a bottom plan view of a sanitary napkin according to the present invention.

Referring now to FIGS. 2 and 3, the portion of the outer surface of backsheet 18 that is generally in vertical registration with absorbent core 16 is provided with central absorbent pad adhesive 20. Central absorbent pad adhesive 20 provides an adhesive attachment means for securing central absorbent pad 12 to the crotch portion of a undergarment. Any adhesive or glue used in the art for such purpose can be used herein, with pressure-sensitive adhesive being preferred. Suitable adhesives are Century A-305IV manufactured by the Century Adhesives Corporation and Instant LOK 34-2823 manufactured by National Starch Company. The central absorbent pad adhesive may be the same width as absorbent core, or as shown in FIG. 3 it may be a plurality of relatively narrow stripes. However, the width is not critical and appropriate widths, as well as lengths, can be readily selected by those skilled in the art. The pressure-sensitive adhesive of central absorbent pad adhesive 20 should be covered with central absorbent pad liner 22 to keep the adhesive from drying out and to keep it from sticking to extraneous surfaces prior to use. Any commercially available release liner commonly used for such purposes can be used herein. Nonlimiting examples of suitable release liners are BL30MG-A SILOXE1/0 and BL 30 MG-A SILOX 4/P/O both of which are manufactured by the Akrosil Corporation.

As can be observed from the foregoing, central absorbent pad 12 comprises an absorbent core having an upper surface covered by a fluid pervious body contacting surface (represented in FIG. 2 by topsheet 14) and an opposed liquid impervious surface (represented in FIG. 2 by backsheet 18). It is to be understood that the embodiment illustrated is only one possible embodiment. Other possible embodiments include one in which an absorbent core is essentially completely wrapped with topsheet before it is placed on a backsheet. The absorbent core can also comprise an absorbent layer which possesses sufficient integrity to stand-alone and which is fluid permeable on one surface while the other surface has been treated to render it liquid impervious.

It should be noted that a relatively narrow central absorbent pad 12 is effective because the overall configuration and use of sanitary napkin 10 results in central absorbent pad 12 being maintained in close proximity to the body. Such proximity of central absorbent pad 12 places it precisely where it should be: very near the body at the vaginal opening. Central absorbent pad 12 can then absorb the vast majority of the menstrual fluid (menses) before it has an opportunity to flow along the central absorbent pad 12. As shown in FIG. 1, the absorbent core 16 is generally tapered from a relatively wide second distal end region to a relatively narrow opposite first distal end region so as to conform generally to the wearer's thighs and to be easily conformable to thong undergarment styles.

Although the side edges are shown to continuously converge towards the longitudinal centerline along the length of the sanitary napkin, such is not, per se, critical to the invention provided of course that the first distal end region has a relatively narrow width that is adapted to be comfortably worn in a thong undergarment. Thus, in alternative embodiments (not shown) the width of the absorbent core can vary along the length of the napkin or alternatively the width may be constant over a considerable length of the sanitary napkin (i.e. wherein the side edges are substantially parallel. However, in every embodiment of the present invention, at least a portion of the absorbent core in the second distal end region has a maximum width that is greater than a maximum width of the absorbent core in the first distal end region.

The width of the wider second distal end is generally less than about 75 mm, preferably from about 70 mm to 60 mm. The width of the absorbent core (and concomitantly the width of the sanitary napkin) preferably continuously tapers from the second distal end toward the first distal end, the absorbent core in the first distal end having a maximum width of less than 40 mm, preferably less than about 30 mm along at least one half of a continuous length of the first distal end region, and more preferably the width is between about 15 to 20 mm along a substantial portion of the length of the first distal end region. While the taper is illustrated as being a substantially straight line, other variations are considered to be within the scope of the present invention such as curved or arcuate lines. It is considered an important feature of the present invention that the length of the first distal end region (as measured from the flap to the transverse end of the napkin) does not greatly exceed the maximum width of the first distal end region. Accordingly, the ratio of the length of the first distal end region to the maximum width of the absorbent core in the first distal end region is less than 2, preferably the ratio is less than 1.5 and most preferably the ratio is about 1.25. In a preferred embodiment, the maximum width of the absorbent core in the second distal end is between 60 mm to 75 mm, and is more preferably about 70 mm. It is also considered an important feature of the present invention that the absorbent core has a maximum width in the first distal end region that does not exceed 40 mm along any portion of the length of the first distal end region and does not exceed 30 mm along at least one half of the length of the first distal end region. Preferably the width of the absorbent core adjacent the first transverse end is less than the width of the absorbent core adjacent the flap.

As illustrated in FIGS. 1 and 2, the sanitary napkin 10 has two flaps 24 and 24' extending laterally outward from the longitudinal side edges of the central absorbent pad 12 and define the central region of the sanitary napkin. As used herein, the terminology "central region" and "lateral centerline" refer generally to a region of the central absorbent pad 12 that is intended to be placed in a crotch portion of a wearer's undergarment and is adapted to be in vertical registration with the labia majora of the wearer in use. Thus, for some embodiments of the invention wherein the sanitary napkin is asymmetrical, such as in a product intended for overnight use, the central region and lateral centerline may not be located in the exact geometric center of the central absorbent pad. Nevertheless, the central region of the sanitary napkin is adapted to be in vertical registration with the labia majora of the wearer in use. While it is not necessary that the flaps be mirror images of one another they preferably are. Topsheet 14 forms one surface of flaps 24, 24' while backsheet 18 forms the other surface. In general, the flaps do not require a topsheet to enable them to function properly, but the use of a topsheet is preferred. Flap topsheet can be integral with the central absorbent body, as illustrated, or it can be an independent element; the former being preferred. All of the specific physical properties of the topsheet 14 previously described, apply to any flap topsheet that is used. There is, however, no requirement that the flap topsheet be the same material as the topsheet associated with the central absorbent pad. In one possible embodiment, the flap topsheet may be nonwoven material while the topsheet over the central absorbent pad is an apertured polymeric film. In the embodiment illustrated in FIG. 2, backsheet 18 serves as a backsheet for flaps 24 and 24'. The flaps require a backsheet (or more generally, a liquid impervious materials) to enable them to function properly. The flap backsheet can be integral with the absorbent core liquid impervious surface or they can be independent elements. All of the specific physical properties of the backsheet 18 previously described apply to the flap backsheet.

At least a portion of the outer, garment faceable surface of flap 24, in a region adjacent distal edge 78, is coated with flap adhesive 36. Flap adhesive 36 is an adhesive attachment means which is used to assist in maintaining flap 24 in position after it is wrapped around the edge of the crotch portion of the undergarment as described below. Any adhesive used for central absorbent pad adhesive 20 can be used as flap adhesive 36. Also, flap adhesive 36 is covered with a removable flap release liner 38. Any release liner material used for central absorbent pad release liner 22 can be used for flap release liner 38. The proximal edge of each flap 24, 24' is associated with central absorbent pad 12 along a line of juncture 26. As used herein, the term "line of juncture" refers to any of various curved or straight lines. The line of juncture is typically greater than 5 cm, preferably between 5 cm and 10 cm. Each flap 24, 24' has a distal edge 78 that is remote from the proximal edge (which is defined by the line of juncture 26). It is to be observed that lines of juncture 26 and 26' are the lines along which flaps 24 and 24' are associated with the absorbent core (represented by central absorbent pad 12); as such they represent lines of demarcation between the absorbent core and the flaps.

The sanitary napkin shown in FIG. 1 has a substantially linear line of juncture 26. The precise shape of flap 24, as well as the overall shape of the sanitary napkin 10 can be selected by those skilled in the art without undue experimentation. In the embodiment illustrated in FIG. 1, the flaps are symmetrically disposed along the longitudinal edge of the sanitary napkin.

The sanitary napkin of the present invention, such as the one illustrated in FIGS. 1–3, is utilized by removing the release liners 22 and 38 and 38' and thereafter placing the sanitary napkin in a undergarment. The center region of central absorbent pad 12 is placed in crotch portion (not shown) of the undergarment with one end of central absorbent pad 12 extending towards the front section of the undergarment and the other end towards the back section and with the backsheet 18 in contact with the inner surface of center crotch portion of the undergarment. Central absorbent pad adhesive 20 maintains central absorbent pad 12 in position. The distal portions of flaps 24 and 24' are folded around, respectively, side edges and of the crotch portion of the undergarment. Flap adhesive 36 and 36' secure flaps 24 and 24' in such position, thus, flaps 24 and 24' are each folded over themselves with a portion of the undergarment.

Figure 4:
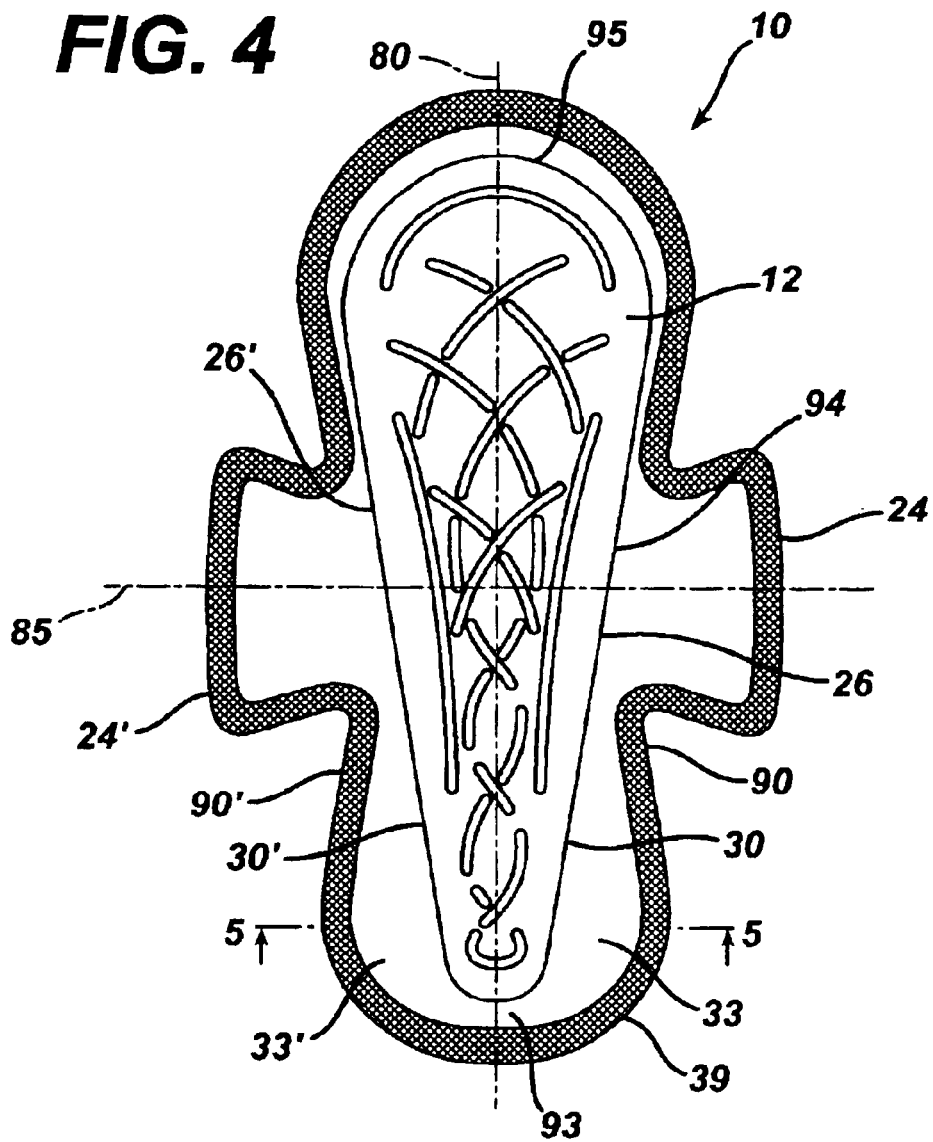
FIG. 4 is a top plan view of another embodiment of the sanitary napkin according to the present invention.
Figure 5:
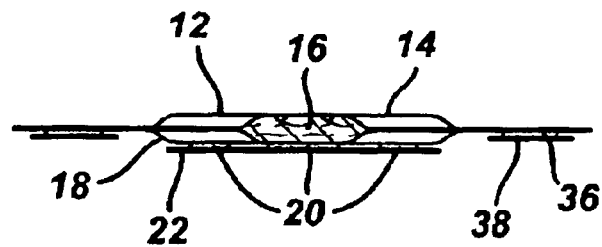
FIG. 5 is a side cut away view of the sanitary napkin of FIG. 4 taken through lines 5—5.
Figure 6:
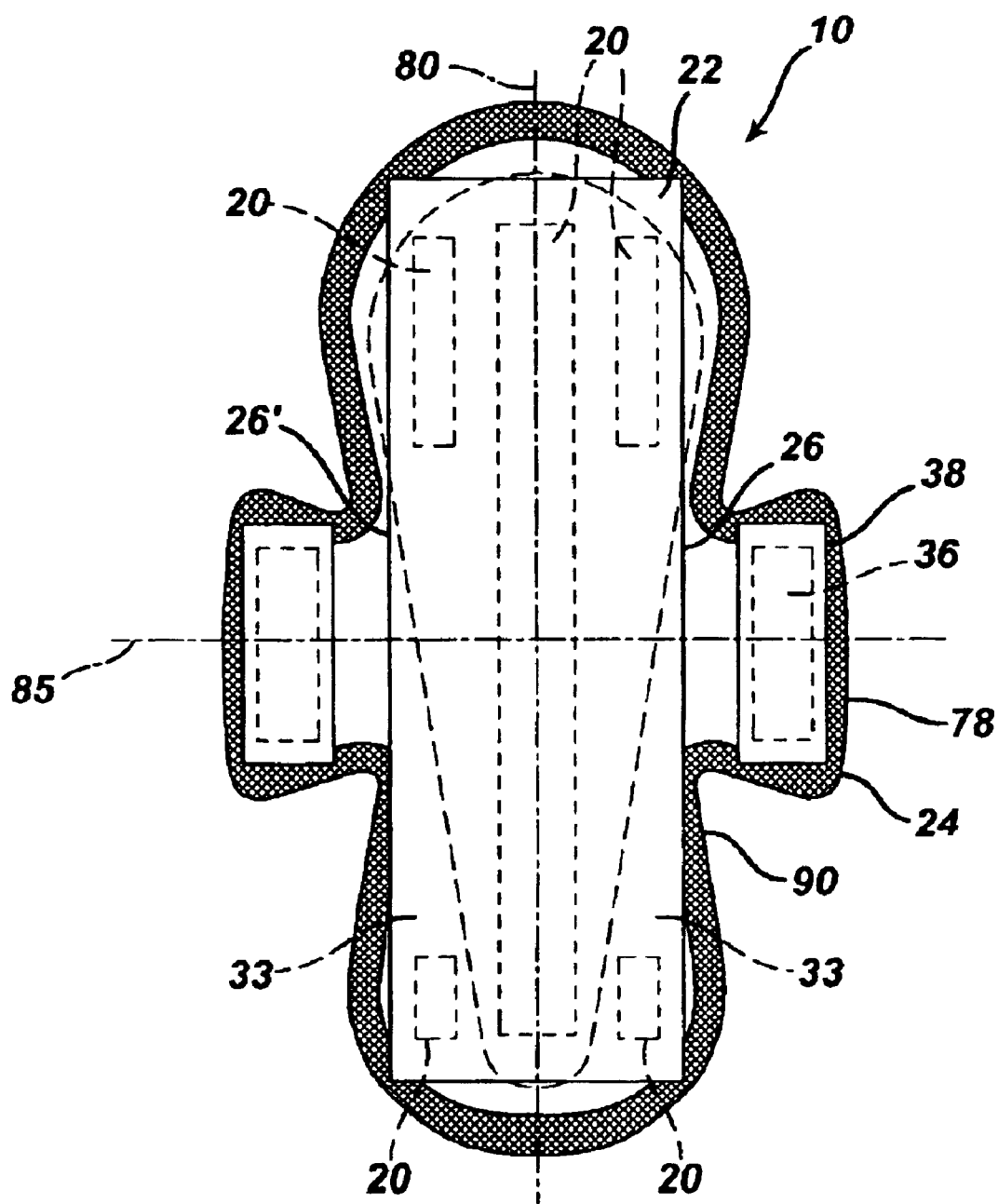
FIG. 6 is a bottom plan view of the sanitary napkin in FIG. 4 according to the present invention.

FIGS. 4–6 illustrate another embodiment of the present invention wherein the same reference numerals identify the same elements as in FIGS. 1–3. In accordance with this embodiment, as shown in FIG. 4, the sanitary napkin 10 is provided with two flaps on each longitudinal side edge, one flap being in the central region and one flap being in the first distal end region. The absorbent core 16 is wider in the second distal end 95 and tapers continuously towards the first distal end 93. By tapering the absorbent core 16 yet maintaining substantially the same width of the other components in the central absorbent pad 12, a pair of opposite preferential bending edges 30, 30' are formed along the edges of the absorbent core in the region from at least the central region 94 to the first distal end 93.

It is to be observed that lines of juncture 26 and 26' are the lines along which flaps 24 and 24' are associated with the absorbent core (represented by central absorbent pad 12); as such they represent lines of demarcation between the absorbent core and the flaps. In the embodiment shown in FIGS. 1 and 3, the lines of juncture 26, 26' are coincident with the preferential bending lines 30, 30 in the central region 94 of the central absorbent pad 12.

What is claimed is:

1. A sanitary napkin adapted to be worn in a thong undergarment comprising a central absorbent pad, the central absorbent pad having;
    a liquid pervious cover layer,
    a liquid impervious barrier layer; and
    an absorbent core between the cover layer and barrier layer having a pair of opposite longitudinal side edges defining therebetween a width dimension, a first transverse end and an opposite second transverse end defining therebetween a length dimension,
    the sanitary napkin having a longitudinal centerline, a lateral centerline, a first distal end region, an opposite second distal end region and a central region intermediate the first distal end region and the second distal end region,
    the sanitary napkin having a flap extending laterally outward from each longitudinal side edge in the central region along a line of juncture, the line of juncture defining the length of the central region, each flap being adapted to fold over a crotch portion of the thong undergarment in use;
    the width of the absorbent core varying along at least a portion of the length of the absorbent core such that the width of the absorbent core in the second distal end region has a maximum value that is greater than a maximum value of the width of the absorbent core in the first distal end region,
    the absorbent core in the first distal end region having a length measured intermediate the central region and the first transverse end, wherein the maximum value of the width of the absorbent core in the first distal end region does not exceed 40 mm along any portion of the length of the first distal end region, the width of the absorbent core in the first distal end region does not exceed 30 mm along at least one half of the length of the first distal end region and wherein a ratio of the length of the first distal end region to the maximum width of the absorbent core in the first distal end region is less than 2.

2. A sanitary absorbent article as defined in claim 1, wherein said ratio is less than 1.5.

3. A sanitary absorbent article as defined in claim 1, wherein said ratio is about 1.25.

4. A sanitary absorbent article as defined in claim 1, wherein the maximum value of the width of the absorbent core in the first distal end is less than 30 mm.

5. A sanitary absorbent article as defined in claim 1, wherein the maximum value of the width of the absorbent core in the first distal end is between 15 mm to 20 mm.

6. A sanitary absorbent article as defined in claim 1, wherein the width of the second distal end region has a maximum value of 70 mm.

7. A sanitary absorbent article as defined in claim 1, wherein each side flap has an adhesive attachment means on a garment faceable side thereof that is adapted to allow a wearer to adhesively affix each side flap to their undergarment in use.

8. A sanitary absorbent article as defined in claim 1, wherein the opposite side edges of the absorbent core converge towards the longitudinal centerline as they extend from the central region toward the first distal end of the sanitary napkin.

9. A sanitary absorbent article as defined in claim 1, wherein the sanitary napkin is provided with two flaps on each longitudinal side edge, one flap extending from the central region of the sanitary napkin and a second flap extending from the first distal end region of the sanitary napkin.

10. A sanitary absorbent article as defined in claim 1 wherein the longitudinal side edges of the absorbent core extend obliquely with respect to the longitudinal centerline in the first distal end region, the width of the absorbent core tapering from the central region to the first transverse end.

* * * * *